United States Patent
Danielsen et al.

(10) Patent No.: US 10,023,905 B2
(45) Date of Patent: Jul. 17, 2018

(54) POLYMERASE DRIVEN NESA

(71) Applicant: GEORGETOWN UNIVERSITY, Washington, DC (US)

(72) Inventors: Mark Danielsen, Germantown, MD (US); Berenice Alfonso, Fairfax, VA (US); Bolor Tumurpurev, Washington, DC (US)

(73) Assignee: Georgetown University, Washington, DC (US)

( * ) Notice: Subject to any disclaimer, the term of this patent is extended or adjusted under 35 U.S.C. 154(b) by 32 days.

(21) Appl. No.: 14/212,124

(22) Filed: Mar. 14, 2014

(65) Prior Publication Data

US 2014/0349285 A1  Nov. 27, 2014

Related U.S. Application Data

(60) Provisional application No. 61/962,304, filed on Mar. 15, 2013.

(51) Int. Cl.
| | |
|---|---|
| C12P 19/34 | (2006.01) |
| C12Q 1/68 | (2018.01) |
| C07H 21/02 | (2006.01) |
| C07H 21/04 | (2006.01) |
| C07H 21/00 | (2006.01) |
| C12Q 1/6844 | (2018.01) |

(52) U.S. Cl.
CPC ................ C12Q 1/6844 (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3
See application file for complete search history.

(56) References Cited

U.S. PATENT DOCUMENTS

| | | | |
|---|---|---|---|
| 6,316,229 B1 | 11/2001 | Lizardi et al. | |
| 2002/0009716 A1* | 1/2002 | Abarzua | C12Q 1/6827 435/5 |
| 2012/0065088 A1 | 3/2012 | Danielsen et al. | |

OTHER PUBLICATIONS

Li et al., Nucleic Acids Research, vol. 36, No. 6, e36 (2008).

* cited by examiner

*Primary Examiner* — Frank Lu
(74) *Attorney, Agent, or Firm* — RatnerPrestia

(57) ABSTRACT

The present invention relates to a novel method for detecting a target polynucleotide having a target sequence, comprising (a) exposing the target polynucleotide to an initiating oligonucleotide; (b) extending the initiating oligonucleotide with an extended sequence complementary to the target sequence; (c) ligating the initiating oligonucleotide sequence with the extended sequence to form a circular oligonucleotide having a nicking endonuclease (NE) recognition/cutting sequence; (d) exposing the circular oligonucleotide to a DNA polymerase and a DNA synthesis primer to synthesize DNA having a NE recognition sequence; (e) exposing the synthesized DNA to a probe having the NE recognition/cutting sequence to form a double stranded DNA having a full NE site; (f) exposing the double stranded DNA to a nicking endonuclease (NE) to cleave the probe; and (g) detecting the cleaved probe. The presence of the cleaved probe indicates the presence of the target polynucleotide.

16 Claims, 3 Drawing Sheets

POLYMERASE DRIVEN NESA

CROSS-REFERENCE TO RELATED APPLICATION

This application claims the benefit of U.S. Provisional Application No. 61/962,304, filed Mar. 15, 2013, the contents of which are incorporated herein by reference in their entireties for all purposes.

FIELD OF THE INVENTION

The invention relates generally to methods for the detection of specific nucleotide sequences and reagents and kits for use in practicing the methods.

BACKGROUND OF THE INVENTION

It is often desirable to detect specific DNA sequences in a mixture of sequences or in a sample that contains DNA and other ingredients. For instance, detection of specific DNA sequences is often used to determine whether a particular bacterium is present in a biological sample. Many techniques can be used including nicking endonuclease signal amplification (NESA), polymerase chain reaction (PCR), quantitative PCR (qPCR), and DNA sequencing. Most techniques use some form of amplification of the DNA to increase sensitivity coupled to an additional method for the identification itself. For instance, NESA may be coupled to a DNA amplification technique. With qPCR, the amplification step occurs at the same time as the detection step. This gives qPCR both sensitivity and speed.

One method of DNA amplification that has been used with NESA is rolling circle amplification (RCA), also called extended NESA (Li et al., Enzymatic Signal Amplification of Molecular Beacons for Sensitive DNA Detection, *Nucleic Acids Res.* 2008; 36(6):e36). In RCA, an oligonucleotide is used to prime a DNA synthesis reaction catalyzed by a strand displacing DNA polymerase. The DNA is a small circle that is continuously copied. In the method described by Li et al., an oligonucleotide was used to bind to the target sequence such that the ends of the oligonucleotide were separated only by a nick. DNA ligase was then used to repair the nick. RCA was performed on the circularized DNA followed by the NESA reaction using molecular beacons specific for the now circular oligonucleotide. The NESA reaction is therefore measuring DNA amplification of the added oligonucleotide rather than directly interacting with the target DNA in a sequence specific manner. This assay is therefore a relatively slow, two-step assay and suffers from a built in background due to circularization that can randomly occur with any oligonucleotide of sufficient length, in the presence of DNA ligase.

There remains a need for reliable and sensitive methods to detect specific nucleotide sequences.

SUMMARY OF THE INVENTION

The present invention relates to methods for detecting a polynucleotide having a unique sequence and related reagents and kits.

According to one aspect of the present invention, a method for detecting a target polynucleotide is provided. The target polynucleotide comprises a target sequence flanked by a first hybridization sequence and a second hybridization sequence. The method comprises (a) exposing the target polynucleotide to an initiating oligonucleotide so that a complex of the target polynucleotide and the initiating oligonucleotide is formed. The initiating oligonucleotide comprises (i) a 5' end sequence complementary to the first hybridization sequence, (ii) a 3' end sequence complementary to the second hybridization sequence, and (iii) a DNA synthesis primer recognition sequence. The complex comprises a first hybridization region formed by the 5' end sequence and the first hybridization sequence and a second hybridization region formed by the 3' end sequence and the second hybridization sequence. The method further comprises (b) extending the initiating oligonucleotide in the complex with an extended sequence, which is complementary to the target sequence; (c) ligating the initiating oligonucleotide sequence with the extended sequence to form a circular oligonucleotide. The circular oligonucleotide comprises a nicking endonuclease (NE) recognition/cutting sequence. The method further comprises (d) exposing the circular oligonucleotide to a DNA polymerase and a DNA synthesis primer having a sequence complementary to the DNA synthesis primer recognition sequence so that a DNA is synthesized. The synthesized DNA comprises a sequence corresponding to the target sequence, a sequence complementary to the DNA synthesis primer recognition sequence, and a NE recognition sequence complementary to the NE recognition/cutting sequence. The method further comprises (e) exposing the synthesized DNA to a probe having the NE recognition/cutting sequence so that a double stranded DNA comprising the probe and the synthesized DNA is formed. The double stranded DNA comprises a full NE recognition site formed by the NE recognition/cutting sequence and the NE recognition sequence. The method further comprises (f) exposing the double stranded DNA to a nicking endonuclease (NE), which can recognize the full NE recognition site and cleave the NE recognition/cutting sequence in the full NE recognition site. The probe in the double stranded DNA is cleaved. The synthesized DNA is dissociated from the probe after the cleavage. The dissociated synthesized DNA comprises a single copy of the target sequence. The method further comprises (g) detecting the cleaved probe. The presence of the cleaved probe indicates the presence of the target polynucleotide.

The target polynucleotide may be a single stranded DNA or RNA, preferably a single stranded DNA. Where the target polynucleotide is a DNA, the initiating oligonucleotide may be extended by a DNA polymerase. Where the target polynucleotide is a RNA, the initiating oligonucleotide may be extended by a RNA reverse transcriptase. The initiating oligonucleotide may have a 5' phosphate or a 5' nucleotide capable of being modified to a 5' phosphate. The target polynucleotide may be obtained from a biological or environmental sample. The target sequence may comprise the NE recognition sequence.

The method may further comprise modifying the NE recognition/cutting sequence in the circular oligonucleotide so that the circular oligonucleotide when in a double stranded DNA is resistant to cleavage by a NE. The NE recognition/cutting sequence may be located anywhere in the circular oligonucleotide. It may be in the initiating oligonucleotide sequence or the extended sequence. It may also span the extended sequence and the initiating oligonucleotide sequence in the circular oligonucleotide.

The NE may be selected from the group consisting of Nb.BbvCI, Nb.BsmI, Nb.BsrDI, Nb.BtsI, nb.Bpu10I, nt.Bpu10I, Nt.AlwI, Nt.BbvCI, Nt.BsmAI, Nt.BspQI, Nt.BstNBI, Nt.CviPII, nt.BSPD61, N.BbvC IA, N.BbvC IB, N.Bst9I, NMIyI, N.SapI, N.BseYI, N.BfiI, NB.mrI, N.FokI, V.BtsCI, N.BspD6I, N.MvaI269I, N.BsrI, R.BbvCI, Nb.SapI-1 (variant 33), Nb.SapI-1, nt.CvQXI.

The initiating oligonucleotide comprises a DNA polymerase stop site. The DNA polymerase stop site may be a RNA linker, a synthetic linker or a modified base.

The method may further comprise modifying the DNA synthesis primer so that the DNA synthesis primer is resistant to exonuclease degradation.

The NE recognition sequence in the synthesized DNA may overlap with the sequence complementary to the DNA synthesis primer recognition sequence.

In the method of the present invention, the target polynucleotide may be detected in a homogenous mixture. Steps (e)-(g) may be repeated. The detection may have a false positive rate of less than 10%.

According to another aspect of the present invention, a kit is provided for each detection method of the present invention. The kit comprises the initiating oligonucleotide, the DNA polymerase, the DNA synthesis primer, the probe and the NE.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
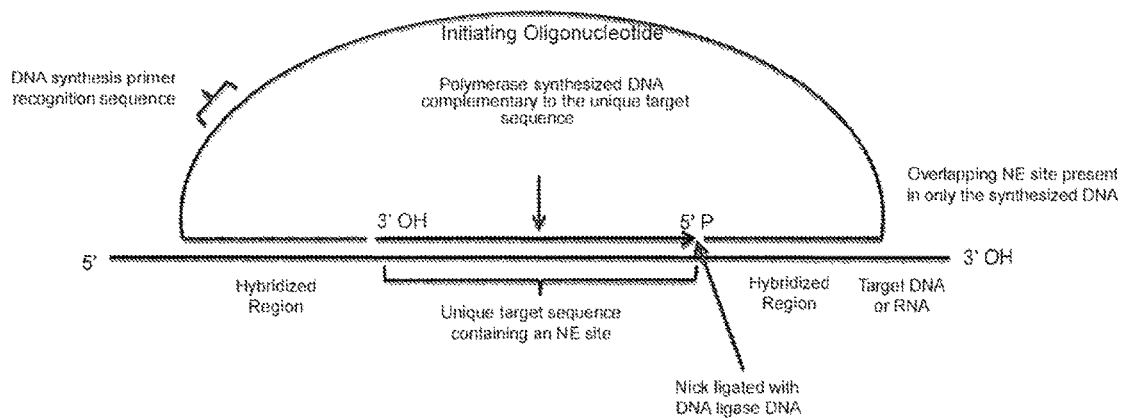
FIG. 1 is a diagram illustrating a first exemplary detection assay according to some embodiments of the disclosed subject matter.

The present invention relates to a novel sensitive method for detecting a specific nucleotide sequence in a polynucleotide based on polymerase driven NESA. The present invention involves redesigning previously known detection assays, for example, extended NESA as described by Li et al., to improve sensitivity, specificity, speed and therefore the utility of the detection assay.

The term "complementary" as used herein refers to the ability of two nucleotide strands, either two DNA strands or a DNA strand and a RNA strand, to form a double stranded duplex having, for example, at least about 80%, 90%, 95%, or 99%, preferably at least about 90%, more preferably at least 95%, most preferably completely 100%, matching purine bases and pyrimidine bases. Two complementary nucleotide strands may have fewer than about 5, 4, 3, 2 or 1 base mismatches.

The term "hybridization" as used herein refers to joining two complementary nucleotide strands to form a duplex of DNA/DNA or DNA/RNA. The two nucleotide strands may be complementary with each other perfectly, i.e., having 100% matching bases, or partially, i.e., having fewer than 100% matching bases. Hybridization conditions can be chosen by a skilled practitioner to provide a desired degree of sequence specific hybridization. In various embodiments, one or more base mismatches may be permitted, or perfect complementarity may be required.

The term "nicking endonuclease (NE)" as used herein refers to any enzyme that cuts one strand of a double stranded DNA (dsDNA) or DNA duplex, having specific complementary nucleotide sequences that form a full NE recognition site. The NE hydrolyzes, cleaves or cuts only one strand of the DNA duplex, leaving the other strand intact and producing a dsDNA molecule nicked, rather than cleaved. NE examples include N.BfiI, N.BseYI, N.Cvi1DORF552P, N.CviNY2BORF703P, N.CviNYs1ORF711P, N.CviNYs1ORF80P, N.FokI, Nb.BbvCI, N.BbvC IA, N.BbvC IB Nb.Bpu10I, Nb.BsaI, Nb.BsmAI, Nb.BsmI, Nb.BspQI, N.BsrI, Nb.BsrDI, Nb.BstNBIP, Nb.BstSEIP, Nb.BtsCI, Nb.BtsI, Nb.MvaI269I, Nb.SapI, Nb.SapI-1 (variant 33), Nb.SapI-1, Nt.AlwI, Nt.BbvCI, Nt.BhaIII, Nt.Bpu10I, Nt.Bpu10IB, Nt.BsaI, Nt.BsmAI, Nt.BsmBI, Nt.BspD6I, Nt.BspQI, Nt.Bst9I, Nt.BstNBI, Nt.BstSEI, Nt.BtsCI, Nt.CviFRORFAP, Nt.CviPII, Nt.CviQII, Nt.CviQXI, Nt.EsaSS1198P, Nt.MlyI, Nt.SapI, V.Aac1083ORF1885P, V.Aac1ORF2169P, V.Aac446ORF1132P, V.Aal15ORF11436P, V.Aap33389ORF1159P, V.AarEBORF6339P, V.Aav19860ORF3517P, V.Aav19860ORF4431P, V.AbaCORFBP, V.AbiC19ORF31P, V.Aca398ORFDP, V.AcrJFORF3583P, V.AdeCPORF3442P, V.AdiB5ORF1248P, V.AexORF1482P, V.Ali4BORF10441P, V.AluIP, V.Ama11ORF370P, V.Ama15272ORF10990P, V.Ama15272ORF10991P, V.Ame32ORF9225P, V.Ame699ORF47315P, V.Ami431ORFAP, V.AmiORF1050P, V.AorK20ORFHP, V.ApeKIP, V.Aph3ORF10150P, V.Apl10ORF12530P, V.Apl1ORFEP, V.ApIORF1202P, V.Apo1ORF396P, V.Asp159ORFCP, V.Asp332ORF2374P, V.AspB510ORF14690P, V.AspBHIP, V.AspBHORF354P, V.AspDG881ORFDP, V.AspFAAORF3152P, V.AspHGB5ORF103P, V.AspJSORF2196P, V.Ast17244ORF884P, V.AstTAV1ORF308P, V.Asu91ORF8785P, V.AveB565ORF2537P, V.AviS4ORF2742P, V.Awo1030ORF18570P, V.Awo1030ORF6460P, V.Axy54ORF1197P, V.Bam10ORF1848P, V.BamFORF3751P, V.BamLL3ORF4074P, V.BamTA208IIP, V.BamXH7ORF4070P, V.Bbr149ORF466P, V.BceMCORF12P, V.BchIP, V.Bcl12056ORF1456P, V.Bdi11568ORFDP, V.BerXPORFBP, V.Bfa27ORFAP, V.BfaDORF26030P, V.BfrYORF3681P, V.BglBGRORF1510P, V.BinAORF2679P, V.Bli1904IIP, V.BmuSORF1526P, V.BokCORFAP, V.BokEORFCP, V.BphAH2ORF35P, V.BphKL3ORFAP, V.Bpr316ORF1914P, V.Bps1106ORF3681P, V.Bps668ORF3504P, V.Bps6ORF3734P, V.Bps7210ORFGP, V.BpyCH67ORFCP, V.Bsa18170ORF1534P, V.BsaDD2ORF3505P, V.BspBTAORF1159P, V.BspCCORF824P, V.BspD20ORF1123P, V.BspFAAORF965P, V.BspH160ORF5810P, V.BsqMORFCP, V.BssHIIIP, V.BsuPORF2033P, V.BsuRIP, V.BsuS2ORFAP, V.BteBS001ORF30563P, V.Bth4ORFHP, V.Bwa316ORF161P, V.Cab13497ORF2004P, V.CacDORF1414P, V.CacDORF8539P, V.CagORF1377P, V.CagORF452P, V.CakORF2727P, V.CamY19DcmP, V.CauJORF2921P, V.Cbo20582ORFAP, V.CcaGD7ORF8530P, V.CcrMORF3626P, V.CcrNAORF1P, V.CfrCORF1922P, V.Cgi13127ORF2868P, V.Cgi13127ORF2948P, V.Cha18680ORF3698P, V.Cho381ORF56P, V.CkoORF981P, V.Ckr177ORF2643P, V.CliKTORF6704P, V.CnuS64ORFDP, V.CphBORF1413P, V.CphORF83P, V.CpiORF2562P, V.Cro168DcmP, V.Csa291ORF5850P, V.Csa894ORF1237P, V.CsaE899ORF17899P, V.CsaES15ORF1468P, V.CseUORF4113P, V.CseUORF449P, V.Csp1363ORFAP, V.CspA1ORF4656P, V.CspAP07ORF1713P, V.CspAP07ORF4746P, V.CspC61ORFAP, V.CspHMORF22030P, V.CspK31ORF4756P, V.CspSSORF21960P, V.CspYORF3160P, V.Csy14163ORF3275P, V.CsyAORFFP, V.CsyORF1631P, V.CthORF1749P, V.CtuORF26770P, V.Cvi110AORF894P, V.Cvi1DORF703P, V.Cvi2s1ORF718P, V.CviCVA1ORF901P, V.CviCVM1ORF894P, V.CviCVR1ORF907P, V.CwoDORF5064P, V.CyoORF6602P, V.DacORF1529P, V.DalAKORF4713P, V.Dba4028ORF891P, V.DbaKORF2578P, V.Dde51507ORF807P, V.DdsORF271P, V.DfrJJORF170P, V.DgoI0ORF36P, V.DhyLam5ORF160184P, V.DjaA8ORFAP, V.DloTORF2919P, V.Dma21211ORF843P, V.Dmc5ORF260P, V.Dmc8ORF290P, V.Dmi345ORF441P, V.Dni574ORF2704P, V.Dpe19664ORF1635P, V.DspA2ORF3942P, V.DspBAVORF79P, V.DtoTol2ORF4110P, V.DvuORF2842P, V.Eae1509ORFKP, V.Eae2190ORF23110P, V.Eam2158ORF2206P, V.EamBORF2080P, V.EamCORF2153P, V.EasLFDcmP, V.Eba57DcmP, V.EbiEbORF26820P, V.Ebl4481DcmP, V.Ecl13047ORF3242P, V.Ecl9394ORF42030P, V.EclENHKDcmP, V.EclGS1DcmP, V.EclSCFDcmP, V.EclSDMDcmP, V.EclWSU1DcmP, V.EclXA1DcmP, V.Eco042DcmP, V.Eco103DcmP, V.Eco111ORF2542P, V.Eco12579DcmP, V.Eco146ORF7390P, V.Eco15647DcmP, V.Eco15657DcmP, V.Eco15658DcmP, V.Eco15DcmP, V.Eco18DcmP, V.Eco2009DcmP, V.Eco2071DcmP, V.Eco227DcmP, V.Eco236DcmP, V.Eco2482DcmP, V.Eco302DcmP, V.Eco3034DcmP, V.Eco3256DcmP, V.Eco33DcmP, V.Eco3493DcmP, V.Eco3677DcmP, V.Eco4115DcmP, V.Eco4404DcmP, V.Eco4522DcmP, V.Eco4623DcmP, V.Eco4632C1DcmP, V.Eco4632C2DcmP, V.Eco4632C3DcmP, V.Eco4632C4DcmP, V.Eco4632C5DcmP, V.Eco536DcmP, V.Eco54115DcmP, V.Eco54115ORF13458P, V.Eco55989DcmP, V.Eco5905DcmP, V.Eco605DcmP, V.Eco7901DcmP, V.Eco8351DcmP, V.Eco857CDcmP, V.Eco8739DcmP, V.Eco89DcmP, V.EcoAA86DcmP, V.EcoABUDcmP, V.EcoAI27DcmP, V.EcoAPECDcmP, V.EcoB088DcmP, V.EcoB185DcmP, V.EcoBL21DcmP, V.EcoBL21DDcmP, V.EcoBWDcmP, V.EcoCB9615DcmP, V.EcoCE10DcmP, V.EcoCFTDcmP, V.EcoDEC10ADcmP, V.EcoDEC10BDcmP, V.EcoDEC10CDcmP, V.EcoDEC10DDcmP, V.EcoDEC10EDcmP, V.EcoDEC10EORF5014P, V.EcoDEC10FDcmP, V.EcoDEC11ADcmP, V.EcoDEC11BDcmP, V.EcoDEC11CDcmP, V.EcoDEC11DDcmP, V.EcoDEC11EDcmP, V.EcoDEC12ADcmP, V.EcoDEC12BDcmP, V.EcoDEC12CDcmP, V.EcoDEC12DDcmP, V.EcoDEC12EDcmP, V.EcoDEC13ADcmP, V.EcoDEC13BDcmP, V.EcoDEC13CDcmP, V.EcoDEC13DDcmP, V.EcoDEC13EDcmP, V.EcoDEC14ADcmP, V.EcoDEC14BDcmP, V.EcoDEC14CDcmP, V.EcoDEC14DDcmP, V.EcoDEC14DORF3444P, V.EcoDEC15ADcmP, V.EcoDEC15BDcmP, V.EcoDEC15CDcmP, V.EcoDEC15DDcmP, V.EcoDEC15EDcmP, V.EcoDEC1ADcmP, V.EcoDEC1BDcmP, V.EcoDEC1CDcmP, V.EcoDEC1DDcmP, V.EcoDEC1EDcmP, V.EcoDEC2ADcmP, V.EcoDEC2CDcmP, V.EcoDEC2DDcmP, V.EcoDEC2EDcmP, V.EcoDEC3ADcmP, V.EcoDEC3BDcmP, V.EcoDEC3CDcmP, V.EcoDEC3DDcmP, V.EcoDEC3EDcmP, V.EcoDEC3FDcmP, V.EcoDEC4ADcmP, V.EcoDEC4BDcmP, V.EcoDEC4CDcmP, V.EcoDEC4DDcmP, V.EcoDEC4EDcmP, V.EcoDEC4FDcmP, V.EcoDEC5ADcmP, V.EcoDEC5BDcmP, V.EcoDEC5CDcmP, V.EcoDEC5DDcmP, V.EcoDEC5EDcmP, V.EcoDEC5EORF5192P, V.EcoDEC6ADcmP, V.EcoDEC6BDcmP, V.EcoDEC6CDcmP, V.EcoDEC6DDcmP, V.EcoDEC6EDcmP, V.EcoDEC7ADcmP, V.EcoDEC7BDcmP, V.EcoDEC7CDcmP, V.EcoDEC7DDcmP, V.EcoDEC7EDcmP, V.EcoDEC8ADcmP, V.EcoDEC8BDcmP, V.EcoDEC8CDcmP, V.EcoDEC8DDcmP, V.EcoDEC8EDcmP, V.EcoDEC9ADcmP, V.EcoDEC9BDcmP, V.EcoDEC9CDcmP, V.EcoDEC9DDcmP, V.EcoDEC9EDcmP, V.EcoDH1DcmP, V.EcoDH1JDcmP, V.EcoDHDcmP, V.EcoDi14DcmP, V.EcoDi2DcmP, V.EcoE24377DcmP, V.EcoEC106DcmP, V.EcoEDDcmP, V.EcoETECDcmP, V.EcoFlDcmP, V.EcoFVDcmP, V.EcoG5101DcmP, V.EcoGDcmP, V.EcoH2687DcmP, V.EcoHSDcmP, V.EcoIAI39DcmP, V.EcoIAIDcmP, V.EcoJ53DcmP, V.EcoK2HCFDcmP, V.EcoK88DcmP, V.EcoKDcm, V.EcoKO11DcmP, V.EcoKO157DcmP, V.EcoLF82DcmP, V.EcoLSU61DcmP, V.EcoMDS42DcmP, V.EcoNA114DcmP, V.EcoO127DcmP, V.EcoO157Dcm2P, V.EcoO157DcmP, V.EcoO26DcmP, V.EcoO78DcmP, V.EcoO81ORFFP, V.EcoP12bDcmP, V.EcoP4DcmP, V.EcoS88DcmP, V.EcoSCI07DcmP, V.EcoSE11ORF2191P, V.EcoSECDcmP, V.EcoTWDcmP, V.EcoUMNDcmP, V.EcoUTDcmP, V.EcoW3110DcmP, V.EcoWDcmP, V.EcoX21DcmP, V.EcoXHDcmP, V.EcyORF20750P, V.EelORF1793P, V.EhaORF1244P, V.EicORF1483P, V.Emo25706DcmP, V.EpyKORF1599P, V.EpyORF14880P, V.EreORF163P, V.EsaCIORFJP, V.EsaD1ORFBP, V.EsaMIORFFP, V.EsaNPORF61P, V.EsaPCHORFIP, V.EsaPCHORFOP, V.EsaPCHORFR1P, V.EsaPCORFDP, V.EsaSS12P, V.EsaSS1346P, V.EsaSS1353P, V.EsaSS13P, V.EsaSS1810P, V.EsaSS1815P, V.EsaSS1816P, V.EsaSS1921P, V.EsaSS192P, V.EsaSS2016P, V.EsaSS20P, V.Esi703ORF17980P, V.Esi703ORF6770P, V.Esp617ORF32150P, V.Esp638ORF2551P, V.EspAg1ORF11829P, V.EspLSJC7ORFAP, V.EspNAPORF13638P, V.EspSST3DcmP, V.EvePORF1844P, V.FacORFFP, V.Fal35896ORF1155P, V.FjoUWORF652P, V.Fpr3ORF9540P, V.FspEUIORF6953P, V.FspF52ORF10278P, V.GbrORF1453P, V.GbrORF534P, V.GdiPAIORF3776P, V.GhaYORF3118P, V.GloSZORF298P, V.Gne59395ORF19667P, V.Gob174ORFHP, V.GobORF756P, V.GpoVH2ORF1720P, V.Gsp412ORF3572P, V.Gsp52ORF3613P, V.GspFRCORF711P, V.GspM18ORF518P, V.GsuKNORF1327P, V.Gxi3C1ORF1475P, V.HarORF1841P, V.HchORF5719P, V.HchORF6653P, V.Hde5ORF1166P, V.HelORF4398P, V.HhaSLORF414P, V.HluP612ORFBP, V.HmoORF2858P, V.HmuDORF450P, V.HpaIIP, V.HruXH70ORF3021P, V.Hsa1ORF39130P, V.HspSORF226P, V.HstS18214ORFAP, V.IloORF2528P, V.Iva225ORF169P, V.JspCORF2858P, V.JspHORF275P, V.KkoORF1707P, V.Kox114921DcmP, V.Kox1686DcmP, V.Kox718DcmP, V.KoxM5a1Dcm2P, V.Kpn1084ORF1803P, V.Kpn11286ORF34490P, V.Kpn19097ORFFP, V.Kpn214ORFIP, V.Kpn2242ORF15105P, V.Kpn3210ORFGP, V.Kpn342ORF1851P, V.Kpn512ORF516P, V.KpnEcl8ORF30111P, V.KpnK2044ORF3560P, V.KpnK26ORF2069P, V.KpnK28ORF5117P, V.KpnLZORFDP, V.KpnMORF2428P, V.KseKMORF35700P, V.KseKMORF37940P, V.KseKMORF57860P, V.KstORFOP, V.KvaAtORF1679P, V.KveORF1127P, V.KveORF4264P, V.KvuWSHORF243P, V.KvuWSHORF254P, V.KvuY25ORF698P, V.KvuY25ORF709P, V.Lac30ORF10930P, V.LamGRLORF11224P, V.Lba2146ORF1320P, V.Lba8157ORF1878P, V.Lde2038ORFAP, V.LdeBBORF1147P, V.LfeML04ORF2182P, V.LhoHORF3244P, V.Lil21528ORF2765P, V.Lin60BORF1315P, V.Llo4968ORF1121P, V.Lpn43290ORF1037P, V.LpnFORF1078P, V.LpnLORF145P, V.LpnPORF1236P, V.MabM156ORFCP, V.Mac2ORF159P, V.Mac2ORFAP, V.MaqORF1714P, V.MauSORF1747P, V.MboM24ORFCP, V.MbuDORF1539P, V.Mca5402ORF1477P, V.McaTIP, V.Mci1271ORF2775P, V.Mfo14469ORF9068P, V.Mha44199ORFAP, V.Mhy49840ORF3709P, V.Min198ORFDP, V.Mma10ORF3057P, V.Mma501ORF4139P, V.Mma79ORFAP, V.MmaGORF278P, V.MmaM172ORFIP, V.MmaMORFC170P, V.MmoKTORF102P, V.MmoSC01ORF3004P, V.MnoORSORF3920P, V.MnoORSORF4984P, V.MnoORSORF7048P, V.Mpa17ORFEP, V.MpaOBBPORFBP, V.Mpe11571ORF2163P, V.MphNM1ORF11490P, V.MpoORF1847P, V.Mro3ORF937P, V.Msa21150ORFGP, V.MsiBL2ORF547P, V.Msp39149ORF5613P, V.Msp49242ORF2623P, V.MspJIP, V.MspKMSORF833P, V.MspL5ORF6093P, V.MspMCSORF817P, V.MspS1ORF46570P, V.MspSC2ORF1734P, V.Mst14675ORF4338P, V.Mst14675ORF5949P, V.MstS30ORFFP, V.Mte37ORF245P, V.MthHORF495P, V.MthTI, V.MtrOB3ORF1773P, V.MvuORF1177P, V.Mxa6833447ORFGP, V.Mxa6833447ORFHP, V.MxaDKORF3598P, V.MyaPS01ORFAP, V.NaeIP, V.Nal2165ORF4531P, V.Nbr1ORF1030P, V.Nbr1ORF31875P, V.Nbr700358ORF27846P, V.Nbr700358ORFAP, V.NcyGUH2ORF207P, V.NfaORF2340P, V.Nfl114ORF805P, V.NflHIIP, V.Ngo14ORF153P, V.Ngo8107ORF1557P, V.Ngo8107ORF336P, V.NgoAXIII, V.NgoAXIV, V.NgoNCORF1961P, V.NgoNCORF450P, V.NhaXORF2515P, V.NhoORF760007P, V.NinC115ORF10163P, V.Nla640ORF15070P, V.NlaCORFGP, V.NlaL17ORFAP, V.NlaY92ORF16400P, V.Nme108ORFFP, V.Nme108ORFNP, V.Nme1207ORFNP, V.Nme13091ORF1925P, V.Nme14902ORF1495P, V.Nme14902ORF1904P, V.Nme1568ORF1879P, V.Nme18ORF1992P, V.Nme18ORF679P, V.Nme198ORF1728P, V.Nme2136ORF1906P, V.Nme2136ORF675P, V.Nme2594ORF142P, V.Nme355ORF1942P, V.Nme6190ORF1345P, V.Nme6190ORF1926P, V.Nme8013ORF2212P, V.Nme961ORF1427P, V.Nme961ORF1951P, V.NmeA153ORF2278P, V.NmeAIP, V.NmeDIP, V.NpoORFAP, V.NsiORF1472P, V.NskFORFDP, V.Nsp12ORF4661P, V.Nsp314ORF1048P, V.NspAR2ORF7940P, V.NspJSORF2284P, V.NspPP1YORF3725P, V.Oba1ORF2988P, V.ObaTAVORF713P, V.Oho17368ORF1447P, V.OihORF3341P, V.OprORF89P, V.Pac4875ORF950P, V.Pac4ORF808P, V.Pae56ORFBP, V.PaeIMORF3201P, V.PaeS1ORFAP, V.PaeXMGORFDP, V.PagIG1DcmP, V.Pal29ORF3490P, V.Pan13355DcmP, V.Pan13DcmP, V.Pan5342DcmP, V.PanB19DcmP, V.PanLMGDcmP, V.Pde1222ORF2061P, V.PgaANG1ORFBP, V.PheORF931P, V.PluTORF338P, V.PmaASORF4322P, V.PmaEXORF251P, V.PmaMORF378P, V.Pmu20ORFCP, V.PogORF508P, V.Ppa514ORF3468P, V.Ppa700821ORF351P, V.Ppu3267ORF10615P, V.PpuB62ORFCP, V.PpuBORFFP, V.PpuGBORF4748P, V.PpuGBORF526P, V.PpuIDORFAP, V.PpuWORF680P, V.Pru23ORF361P, V.PsaKCT1ORFDP, V.Psp102ORF4900P, V.Psp16ORF2276P, V.Psp1860ORF1393P, V.Psp1860ORF1413P, V.Psp1DcmP, V.Psp24ORF5007P, V.Psp343DcmP, V.Psp393ORF831P, V.Psp49ORF3511P, V.Psp531ORF3277P, V.Psp5639ORFBP, V.Psp67ORF1762P, V.Psp74ORF4368P, V.Psp836ORF117P, V.Psp84ORF674P, V.Psp9DcmP, V.PspGM60ORF542P, V.PspHYSORFBP, V.PspSc1DcmP, V.PspUW4ORF4188P, V.Pst14405ORFKP, V.Pst18206ORF2235P, V.PstT13ORFEP, V.PsuGORF1606P, V.PsuGORF2195P, V.PsuNIP, V.Psy4ORF4606P, V.PvaCDcm2P, V.PviORF77P, V.PvoV453ORF1615P, V.PzuORF2431P, V.PzuORF3358P, V.Ral7ORF708P, V.Raq78ORF3962P, V.Rba16ORFBP, V.RbaY4ORF1825P, V.RbaY4ORF3688P, V.Rca13941ORF1389P, V.Req1035ORF2900P, V.RerPR4ORF3260P, V.RetORF108P, V.RfeDORF3077P, V.RgeCBSORFEP, V.RgeMORFGP, V.Rim300ORF18144P, V.Rin50ORF12000P, V.RlaIP, V.Rle1325ORF7069P, V.Rli149ORF28190P, V.RmaFORFGP, V.RopB4ORF40810P, V.RopB4ORF60P, V.Rpa18ORF4309P, V.RpaB53ORF3252P, V.RpaBORF4309P, V.RpaBORF4366P, V.RpaDX1ORF277P, V.RpaDX1ORF3623P, V.RpaHORF3325P, V.RpaHORF472P, V.RpaORF349P, V.RpaTORF352P, V.RpaTORF3927P, V.RpiDORF206P, V.RpyAK37ORF17940P, V.RshIP, V.RsoCMR15ORF21P, V.RsoORF3438P, V.RsoPSIORF12P, V.Rsp10ORF2229P, V.Rsp115ORF6300P, V.Rsp122ORF4435P, V.Rsp142ORF3930P, V.Rsp17029ORF3387P, V.Rsp18449ORF580P, V.Rsp18863ORF140P, V.Rsp217ORFDP, V.Rsp24678ORF3635P, V.RspDK17ORFAP, V.RspJVH1ORF5402P, V.RspKDORF4111P, V.RspP14ORFAP, V.RspP14ORFGP, V.RspRORF4149P, V.RspRSORF4109P, V.RspTW15ORFCP, V.RspWS8NORF6405P, V.RtoL2ORF14860P, V.RtoL2ORF32080P, V.RvaDORF1484P, V.RxyORF2232P, V.Sac10332ORF60P, V.SacTPYORF66P, V.Saf8902ORF875P, V.SamORF281P, V.Saz14600ORF1362P, V.SbiORF5770P, V.SbiORF5788P, V.Sbo12419DcmP, V.Sbo227DcmP, V.SboBSDcmP, V.Sca3403ORF1820P, V.Sch3882ORFMP, V.SchL1ORF2001P, V.SchL1ORF2414P, V.SdySDcmP, V.Sen1010DcmP, V.Sen1018DcmP, V.Sen1117DcmP, V.Sen116DcmP, V.Sen12DcmP, V.Sen1319DcmP, V.Sen131DcmP, V.Sen1392DcmP, V.Sen1427DcmP, V.Sen1438DcmP, V.Sen1441DcmP, V.Sen1444DcmP, V.Sen1445DcmP, V.Sen1455DcmP, V.Sen1457DcmP, V.Sen14970DcmP, V.Sen1543DcmP, V.Sen1558DcmP, V.Sen1559DcmP, V.Sen1565DcmP, V.Sen1566DcmP, V.Sen1575DcmP, V.Sen1580DcmP, V.Sen1594DcmP, V.Sen1616DcmP, V.Sen1660DcmP, V.Sen1725DcmP, V.Sen1729DcmP, V.Sen1745DcmP, V.Sen1747DcmP, V.Sen1757DcmP, V.Sen1791DcmP, V.Sen1795DcmP, V.Sen17DcmP, V.Sen1808DcmP, V.Sen1810DcmP, V.Sen1811DcmP, V.Sen1831DcmP, V.Sen18569DcmP, V.Sen1882DcmP, V.Sen1884DcmP, V.Sen18DcmP, V.Sen191Dcm2P, V.Sen191DcmP, V.Sen19443DcmP, V.Sen19593DcmP, V.Sen196DcmP, V.Sen1976DcmP, V.Sen199Dcm2P, V.Sen199DcmP, V.Sen20037DcmP, V.Sen21538DcmP, V.Sen21550DcmP, V.Sen2217DcmP, V.Sen225101DcmP, V.Sen22704DcmP, V.Sen22DcmP, V.Sen23580DcmP, V.Sen23701DcmP, V.Sen240DcmP, V.Sen2490DcmP, V.Sen2558DcmP, V.Sen2625DcmP, V.Sen2651DcmP, V.Sen2659DcmP, V.Sen268DcmP, V.Sen26DcmP, V.Sen290DcmP, V.Sen29188DcmP, V.Sen2977DcmP, V.Sen29DcmP, V.Sen30663DcmP, V.Sen3076DcmP, V.Sen3079DcmP, V.Sen308DcmP, V.Sen316DcmP, V.Sen317DcmP, V.Sen33953DcmP, V.Sen3404DcmP, V.Sen35185DcmP, V.Sen3618DcmP, V.Sen3668DcmP, V.Sen377DcmP, V.Sen37978DcmP, V.Sen37DcmP, V.Sen3944Dcm2P, V.Sen3991DcmP, V.Sen39DcmP, V.Sen4018DcmP, V.Sen403DcmP, V.Sen407DcmP, V.Sen41563DcmP, V.Sen41565DcmP, V.Sen41566DcmP, V.Sen41573DcmP, V.Sen41579DcmP, V.Sen4220DcmP, V.Sen424DcmP, V.Sen433DcmP, V.Sen436DcmP, V.Sen4441DcmP, V.Sen4481DcmP, V.Sen44DcmP, V.Sen4647DcmP, V.Sen46DcmP, V.Sen474DcmP, V.Sen480DcmP, V.Sen483ORF1127P, V.Sen486DcmP, V.Sen487DcmP, V.Sen4941DcmP, V.Sen5078DcmP, V.Sen50DcmP, V.Sen537DcmP, V.Sen543DcmP, V.Sen5621DcmP, V.Sen5646DcmP, V.Sen567DcmP, V.Sen580DcmP, V.Sen618DcmP, V.Sen620DcmP, V.Sen6211DcmP, V.Sen6297DcmP, V.Sen633DcmP, V.Sen640631DcmP, V.Sen6482DcmP, V.Sen653DcmP, V.Sen6670DcmP, V.Sen669DcmP, V.Sen66DcmP, V.Sen6DcmP, V.Sen7015DcmP, V.Sen703DcmP, V.Sen709DcmP, V.Sen7307DcmP, V.Sen7308Dcm2P, V.Sen7308DcmP, V.Sen7927DcmP, V.Sen798DcmP, V.Sen895DcmP, V.Sen899DcmP, V.Sen8blDcmP, V.Sen9120DcmP, V.Sen9163DcmP, V.Sen9317DcmP, V.Sen956DcmP, V.Sen968DcmP, V.Sen9845DcmP, V.SenA50DcmP, V.SenAKUORF818P, V.SenARA23DcmP, V.SenAZDcmP, V.SenB182DcmP, V.SenCHS44DcmP, V.SenCHS4DcmP, V.SenCORF1995P, V.SenCVMDcmP, V.SenDCORF1249P, V.SenEORF1018P, V.SenG9184DcmP, V.SenGORF1063P, V.SenHDcmP, V.SenHWS51DcmP, V.SenJDcmP, V.SenLA5DcmP, V.SenN202DcmP, V.SenNDcmP, V.SenPT23DcmP, V.SenRKSORF1723P, V.SenSARB17DcmP, V.SenSDDcmP, V.SenSE10DcmP, V.SenSE151DcmP, V.SenSE8aDcmP, V.SenSG9DcmP, V.SenSL491DcmP, V.SenSL909DcmP, V.SenSL913DcmP, V.SenSLDcmP, V.SenSPBDcmP, V.SenSS209DcmP, V.SenST0208DcmP, V.SenT1DcmP, V.SenUJ308ADcmP, V.SenUK1DcmP, V.SenWDcmP, V.SerORF1557P, V.Ses44229ORF12230P, V.Ses44229ORF73890P, V.Sfl2DcmP, V.Sfl33331ORF1288P, V.Sfl33331ORF2970P, V.Sfl8401DcmP, V.SflFDcmP, V.SflM90TDcmP, V.SflTDcmP, V.Sfr103ORF610P, V.SfuMORF2797P, V.SfuMORF3853P, V.SghWORFDP, V.Sgl1027ORFDP, V.Sgr13350IIP, V.Sgr45ORF2971P, V.SgrTORF2918P, V.SgrTORFEP, V.Shy5008ORFCP, V.ShyTL1ORFEP, V.SinB90AORF12314P, V.SinB90AORF4622P, V.Sme4ORF23P, V.SmeGR4ORF23P, V.SmeORF3763P, V.SnaDORF1617P, V.Sno43541ORF1028P, V.Spr568ORF573P, V.SptAORF878P, V.Ssc87ORF57141P, V.SseARORF4012P, V.SshL3AORF16499P, V.Sso40738ORFGP, V.Sso46DcmP, V.Sso53GDcmP, V.Ssp18395ORFDP, V.Ssp4354ORF2301P, V.SspAS12ORF510P, V.SspAS13ORF510P, V.SspAS9ORF510P, V.SspS17ORF3425P, V.SspSYK6ORF26790P, V.SstS4ORFFP, V.StrCORF568P, V.StyCDcmP, V.StyLT2DcmP, V.StyTDcmP, V.SusEORF1689P, V.Svi4113ORF568P, V.SwiDP58ORFGP, V.SwiRWORF2535P, V.SxiS187ORFHP, V.SziORF15388P, V.TacORF961P, V.TagYORF881P, V.TarIpORFHP, V.TcoKWC4ORF3624P, V.TcoKWC4ORF809P, V.TcuORF4863P, V.TdeDORF1810P, V.TneIP, V.TsaSORF4122P, V.Tsp970ORF4585P, V.TspA62ORF2259P, V.TspCL1ORF1080P, V.TspJC4ORFAP, V.TspL4CORFAP, V.TspMIP, V.TspMZORF2371P, V.TspRIP, V.Uba827905ORFAP, V.UbaHFDcmP, V.UbaMDORFJ11P, V.UbaMDORFP1P, V.UbaMDORFX8P, V.UbaMDORFY4P, V.UbaN47ORF13040P, V.Umc3GORF15P, V.UtbRsORFKP, V.VeiORF1175P, V.VmaORF7710P, V.Vsp313ORF1722P, V.XnePORF3668P, V.XorIIP, V.XorKIP, V.YfrORFAP, other nicking enzymes in the REBASE database (http://rebase.neb.com), and any restriction enzyme that is modified to cut just one strand of DNA, i.e., nick DNA. A nucleotide sequence in a full NE recognition site that is subject to cut or cleavage by an NE is hereinafter referred to as the NE recognition/cutting sequence while the nucleotide sequence in the full NE recognition site that is not subject to cut or cleavage by the NE is hereinafter referred to as the NE recognition sequence.

The term "target polynucleotide" used herein refers to any type of single stranded DNA or RNA. A double stranded DNA may be converted into a single stranded DNA for use in the detection method according to the present invention. The target polynucleotide may be of any length. For example, the target polynucleotide may have at least about 25, 50, 100, 200 or 500 nucleotides. The target polynucleotide may be genomic DNA or RNA; denatured DNA or RNA; synthesized DNA or RNA; or DNA or RNA that has been purified. The target polynucleotide may be part of a heterogeneous sample, e.g., a biological or environmental sample. A biological sample is a sample obtained from a biological source, for example, serum, ascites fluid, cerebrospinal fluid, amniotic fluid, synovial fluid, pleural fluid, saliva, sputum, stool, urine, semen, tissue, biopsies, swabs, and the like from human and non-human sources. An environmental sample is a sample obtained from an environmental source such as air (aerosol sampling) water, soil and the like.

The target polypeptide comprises a target sequence flanked by two hybridization sequences, one on each side. The target sequence may have about 5-50, preferably about 5-20, more preferably about 5-10 nucleotides, and may be identified uniquely. The hybridization sequences may be of any length, preferably at least about 10, 20 or 50 nucleotides. The target sequence may comprise an NE recognition sequence. The NE recognition sequence may be close to one or both of the hybridization sequences, for example, within about 50, 20, 10 or 5 nucleotides.

The term "initiating oligonucleotide" used herein refers to a single stranded DNA having fewer than about 500, 200, 100 or 50 nucleotides. The initiating oligonucleotide comprises a 5' end sequence that is complementary to the first hybridization sequence and a 3' end sequence that is complementary to the second hybridization sequence. Preferably, the initiating oligonucleotide is of sufficient length to form an open circle when hybridized to the target polynucleotide via the hybridization sequences. It also comprises one or more DNA synthesis primer recognition sequences. The DNA synthesis primer recognition sequences may be the same or different, preferably the same.

The present invention provides a method for detecting a target polynucleotide, comprising (a) exposing the target polynucleotide to an initiating oligonucleotide to form a complex of the target polynucleotide and the initiating oligonucleotide; (b) extending the initiating oligonucleotide in the complex with an extended sequence; (c) ligating the initiating oligonucleotide sequence with the extended sequence to form a circular oligonucleotide comprising an NE recognition/cutting sequence; (d) exposing the circular oligonucleotide to a DNA polymerase and a DNA synthesis primer to synthesize a DNA having an NE recognition sequence; (e) exposing the synthesized DNA to a probe having an NE recognition/cutting sequence to form a double stranded DNA having a full NE recognition site; (f) exposing the double stranded DNA to a nicking endonuclease (NE) to cleave the probe in the double stranded DNA; and (g) detecting the cleaved probe. The presence of the cleaved probe indicates the presence of the target polynucleotide. The detection may have a false positive rate of less than about 10%, 5% or 1%, preferably less than about 5%, more preferably less than about 1%.

In step (a), the target polynucleotide and the initiating oligonucleotide are maintained under conditions permitting the formation of a complex of the target polynucleotide and the initiating oligonucleotide. In the complex, the 5' end sequence of the initiating oligonucleotide is hybridized to one hybridization sequence of the target polynucleotide while the 3' end sequence of the initiating oligonucleotide is hybridized to the other hybridization sequence of the target polynucleotide. The 5' and 3' end sequences may have sufficient length and sequence similarity to allow hybridization of the initiating oligonucleotide to the target polynucleotide.

Upon hybridization, an open circle of the initiating oligonucleotide is formed having a gap between the 5' end and the 3' end. The gap is filled in by the extension of the initiating oligonucleotide by DNA synthesis. The resulting extended sequence is a DNA sequence complementary to the target sequence. The extension may be accomplished a DNA polymerase (e.g. *E. coli* DNA polymerase, Klenow fragment in a buffer) for a DNA target polynucleotide or a reverse transcriptase for a RNA target polynucleotide, which allows DNA synthesis to fill in the gap between the 3' OH group and the 5' phosphate group of the initiating oligonucleotide using the target DNA or RNA as a template. The initiating oligonucleotide may have a 5' phosphate or a nucleotide that can be modified to allow phosphodiester bond formation (e.g. a 5'-OH group that can be phosphorylated with a kinase).

Figure 2:
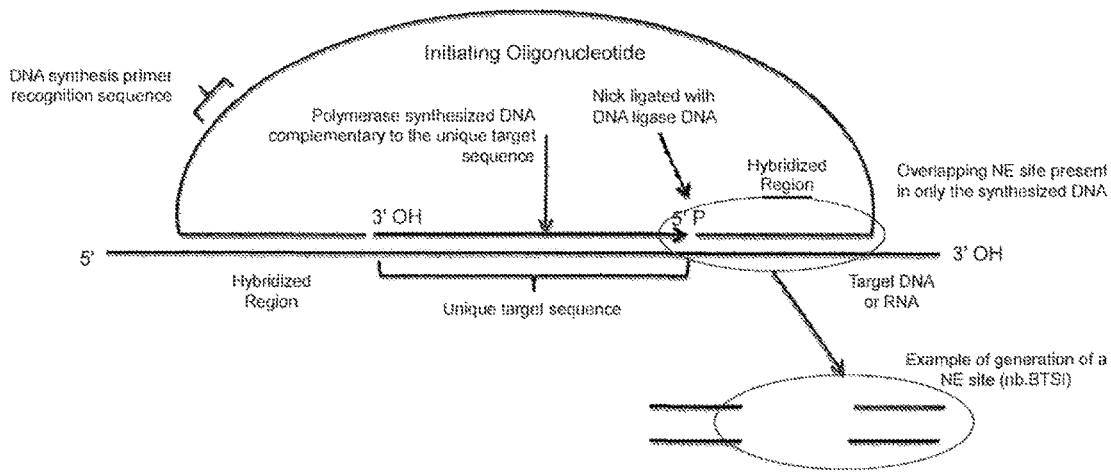
FIG. 2 is a diagram illustrating a second exemplary detection assay according to some embodiments of the disclosed subject matter.
Figure 3:
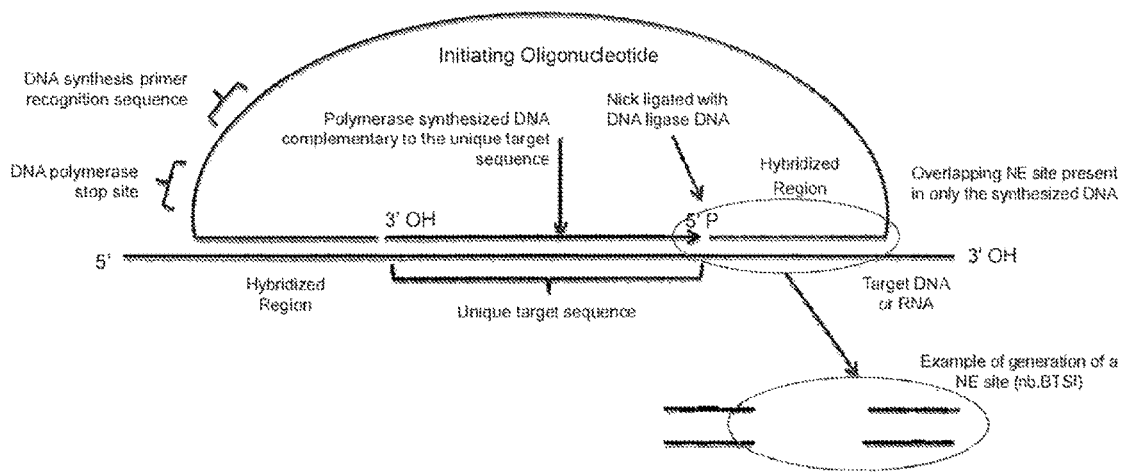
FIG. 3 is a diagram illustrating a third exemplary detection assay according to some embodiments of the disclosed subject matter.

After the extension step, a nick is present between the initiating oligonucleotide and the extended sequence. This nick may be ligated by a DNA ligase, for example, T4 ligase. Upon ligation, a circular oligonucleotide is formed. The circular oligonucleotide comprises the initiating oligonucleotide sequence and the extended sequence. The circular oligonucleotide comprises a nicking endonuclease (NE) recognition/cutting sequence. The NE recognition/cutting sequence may be located any where in the circular oligonucleotide, for example, in the initiating oligonucleotide sequence or the extended sequence. The NE recognition/cutting sequence may also span the initiating oligonucleotide sequence and the extended sequence. For example, the 5' end sequence in the initiating oligonucleotide may be modified to create mismatch of one or more bases with the corresponding hybridization sequence, as long as the stability in the corresponding hybridization region is maintained, resulting in an NE recognition/cutting sequence in the circular oligonucleotide spanning the initiating oligonucleotide sequence and the extended sequence (FIGS. 2 and 3). The NE recognition/cutting sequence in the circular oligonucleotide is subject to cleavage by an NE when hybridized to a complementary sequence forming a full NE recognition site. To improve resistance of the circular oligonucleotide to the NE, the NE recognition/cutting sequence may be modified.

The DNA synthesis primer is a DNA oligonucleotide having a 3' OH residue that allows for DNA synthesis. It has a sequence complementary to the DNA synthesis primer recognition sequence, and hybridizes to the circular oligonucleotide. The DNA synthesis primer may comprise one or more modifications to prevent exonuclease degradation. For instance it may contain phosphorothioate bonds. The DNA synthesis primer may produce an NE site upon extension by DNA polymerase.

In step (d), the circular oligonucleotide, the DNA polymerase and the DNA synthesis primer are maintained under conditions permitting DNA synthesis from the DNA synthesis primer using the circular oligonucleotide as a template. The synthesized DNA comprises a sequence corresponding to the target sequence. Where the target sequence is DNA, the synthesized DNA comprises the target DNA sequence. Where the target sequence is RNA, the synthesized DNA comprises a DNA sequence complementary to the cDNA of the target RNA sequence. The synthesized DNA also comprises a sequence complementary to the DNA synthesis primer recognition sequence and a NE recognition sequence complementary to the NE recognition/cutting sequence.

The probe is a DNA oligonucleotide comprising the NE recognition/cutting sequence. In step (e), the synthesized DNA and the probe are maintained under conditions permitting the formation of a double stranded DNA (dsDNA). The dsDNA comprises a full NE recognition site, which is formed by the NE recognition/cutting sequence in the probe and the NE recognition sequence in the synthesized DNA.

The nicking endonuclease (NE) is capable of recognizing the full NE recognition site in the double stranded DNA and cleaving the NE recognition/cutting sequence in the full NE recognition site. In step (f), the double stranded DNA and the NE are maintained under conditions permitting cleavage of the probe in the double stranded DNA and dissociation of the synthesized DNA from the cleaved probe. The resulting dissociated synthesized DNA comprises a single copy of the target sequence.

The cleaved probe may be detected based on the presence of a shortened DNA probe or the cleavage of a fluorescently labeled probe using techniques known in the art, including poly-acrylamide gel electrophoresis (PAGE), capillary electrophoresis (CE), and fluorescence resonance energy transfer (FRET). While CE is the most sensitive, FRET analysis may be performed in a real-time detection assay. Fluorescent labels and quenchers may be placed anywhere in the probe as long as they do not inhibit the nicking endonuclease (NE). For instance, two fluorescent labels may be used to increase the signal strength, or probes with different spectral characteristics may be used in multiplexing.

There are other ways to detect probe fragments. Optical detection methods may be used including bioluminescence and phosphorescence techniques, with or without resonance transfer (e.g., BRET and PRET). In addition, lanthanide-based energy transfer (LRET) may be used to observe the separation between appropriate labels. Mass Spectroscopy may be used with or without mass spectroscopy tags. Raman Spectroscopy is another option. Indeed, labeling of the probe with a surface enhanced Raman sphere can increase sensitivity many fold. Another way to detect the fragments produced relates to the fact that each cleavage results in a new 3' hydroxyl and a new 5' phosphate. The increasing presence of either can be measured and enzymatic activity calculated.

In the method according to the present invention, a target polynucleotide may be detected in a series of separate steps or in a homogenous mixture, preferably in a homogenous mixture. The homogenous mixture may comprise all the reagents, including the initiating oligonucleotide, the DNA polymerase, the DNA synthesis primer, the probe and the NE. In some embodiments, all reagents are mixed together at the same time at a temperature compatible to all the enzymes to give a homogeneous assay. In other embodiments, the reagents are added step wise in an order in accordance with the present invention. The reaction may be continued until sufficient probe is cleaved.

Steps (e)-(g) of the present method may be repeated. In particular, the synthesized DNA dissociated from a cleaved probe in step (f) may be re-exposed to a probe having the NE recognition/cutting sequence. A double stranded DNA of the probe and the synthesized DNA may be formed, and comprise a full NE recognition site formed by the NE recognition/cutting sequence in the probe and the NE recognition sequence in the synthesized DNA. The double stranded DNA may be exposed to a NE capable of recognizing the full NE recognition site and cleaving the NE recognition/cutting sequence in the full NE recognition site. The probe in the double stranded DNA may be cleaved, and the synthesized DNA may be dissociated from the cleaved probe. The dissociated synthesized DNA remains to comprise a single copy of the target sequence. The cleaved probe detected. Where the presence of the cleaved probe is detected based on fluorescence emission by a cleaved probe, steps (e)-(g) may be repeated until no further increase in fluorescence or when the florescence reaches a threshold value.

According to the present invention, a mechanism has been developed to remove a background signal due to random circularization of an oligonucleotide used to hybridize to a target polynucleotide. This significantly increases the signal to noise ratio of the assay and, more importantly, ensures near 100% confidence in a positive result. For example, where the target sequence contains an NE site, the initiating oligonucleotide may be designed to straddle a region corresponding to the target sequence to remove a background signal due to random circularization of the oligonucleotide. As shown in FIG. 1, the ends of the initiating oligonucleotide are separated by a number of nucleotides, and this region contains an NE site. Where the target sequence is DNA, a DNA polymerase may be used to synthesize this region using the initiating oligonucleotide as a primer and then a DNA ligase to form circular DNA. RCA may be performed but the amplified product contains a region of the target that was not present in the initiating oligonucleotide. Multiple priming sites may be used if desired. Because the NE site is not in the initiating oligonucleotide, it cannot be amplified in subsequent reactions unless it becomes part of the circular DNA during the DNA synthesis reaction. This reduces the expected false positive rate of amplification to a very low level, for example, less than about 10%, 5% or 1%, preferably less than about 5%.

In addition, a method has been developed to introduce an NE site into the circularized DNA that is not present in the oligonucleotide itself. The most advantageous method would be for the NE site to be made de novo by the circularization process itself, i.e., the NE site is not present in either the oligonucleotide or in the target DNA initially but is generated by the reaction.

For example, where the target sequence does not contain an NE site, an NE site may be introduced into the circularized oligonucleotide. The NE site is not present in either the target or the initiating oligonucleotide to start but may be generated by the present method. Instead of an exact match between the initiating oligonucleotide and the target polynucleotide, the initiating oligonucleotide contains one or more mismatches that, when combined with the polymerase fill-in reaction, generates a novel NE site. As showing in FIG. 2, by introducing mutations into one or more of the hybridizing regions, NE sites may be added where they were not present before. This example shows the creation of a nb.BTSI site in the circularized oligonucleotide, which nb.BtsI site is not present in the initiating oligonucleotide or in the target DNA. Mutations may be introduced by point or large mutations as long as the stability in the hybridizing region is maintained. Blue line and bases represent the initiating oligonucleotide. Red line and bases represent the synthesized DNA. Black line and bases represent the target polynucleotide. The mismatched base to create a nb.BTSI site is underlined, in green. The red G is not present in the initiating oligonucleotide. As the reaction has to occur before the NE site is generated in this method, the false positive rate may be reduced to essentially zero, for example, less than about 5%, 1% or 0.5%, preferably less than about 1%. This method opens up most of the target sequences to analysis using NESA. Usually NE sites are relatively rare in DNA limiting the usefulness of NESA especially in targets of limited size such as found in small genomes. The ability to add an NE site also allows the use of any type of nicking endonucleases (NEs). This increases the flexibility of the assay, or the detection method, especially in cases where constraints of buffer composition and/or temperature are present (e.g., in serial, or homogeneous reactions).

Further, the method according to the present invention allows multiple modes of detection of the amplified product, i.e., the synthesized DNA comprising a specific target sequence, providing versatility and built in redundancy. Exemplary modes of detection include, but not limited to, PCR, restriction fragment length analysis, hybridization probes and DNA sequencing. The generation of a novel sequence by, for example, using a mismatch initiating oligonucleotide (FIG. 2), may be detected by NESA, or any method capable of detecting the difference between very similar sequences, for example, with single or multiple nucleotide changes. Detection of a specific DNA amplification product may be accomplished by replacing RCA with strand displacement amplification. The multiple modes of detection of an amplified product provide improved the assay flexibility and allow error checking using multiple measures.

The method according to the present invention ensures that the primary product of DNA synthesis is a single-stranded DNA complementary to the circularized DNA so that down-stream reactions requiring single stranded DNA can occur efficiently. In particular, only the DNA strand complementary to the circular DNA is synthesized efficiently. In RCA, very long single-stranded DNAs are synthesized as the DNA "rolls off" the circular template. Although highly efficient, it does generate a large target for DNA synthesis in the opposite direction due to "random"

priming. In the present method, RCA can be replaced by a new technique, circle-driven multiple displacement amplification.

To prevent RCA, a replication incompatible oligonucleotide modification may be used so that the target is synthesized and then, almost immediately, replication stops. Such replication stop may be created using modified nucleotides or nucleotides that cannot be copied by DNA polymerase (e.g. ribonucleotides, and synthetic linkers). As shown in FIG. 3, a DNA polymerase stop site in the circular oligonucleotide prevents RCA from occurring. The DNA polymerase stop site may consist of any modification that prevents DNA synthesis, including a RNA linker, a synthetic linker, and a modified base.

Figure 4:
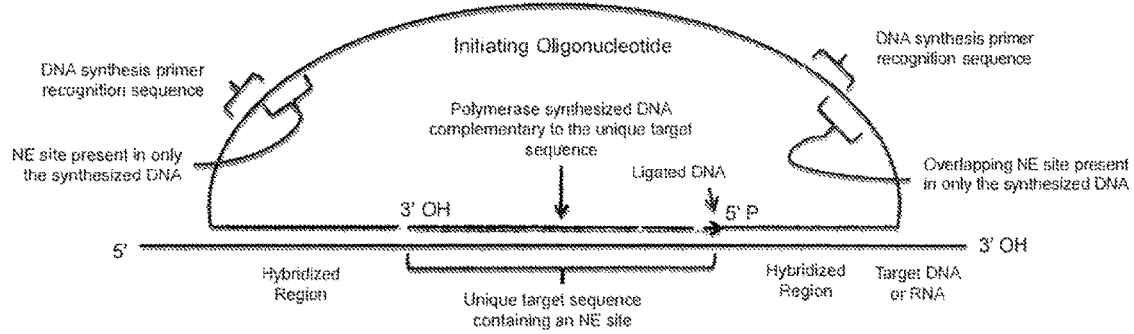
FIG. 4 is a diagram illustrating a fourth exemplary detection assay according to some embodiments of the disclosed subject matter.

To ensure re-initiation of DNA synthesis using the circular DNA as a template, the initiating oligonucleotide may be designed to contain one or more NE sites. These sites may be designed in such a way that only the newly replicated DNA is nicked. The nicked DNA now has a 3' OH group that can act as the primer for additional rounds of DNA synthesis. Because the NE site is regenerated in each round, a new priming site is generated continuously. For example, in re-priming DNA synthesis as illustrated in FIG. 4, an NE site is designed into the initiating oligonucleotide. Preferably, this NE site is not present in the DNA synthesis primer but can be overlapping or located elsewhere. This prevents NE cutting before DNA synthesis occurs. An NE site is acceptable in the primer when the nicked primer remains bound to the circularized DNA. Where a priming system such as this is used, a DNA polymerase stop motif is be optional. Multiple priming sites may be used if desired.

Where only the DNA strand complementary to the circular DNA is synthesized efficiently, generation of double-stranded DNA may be reduced resulting in increased sensitivity; regenerated priming sites may be used for efficient DNA synthesis; and unique replication products may be produced and measured independently (e.g. by size).

According to the present invention, the NESA reaction may be combined with the DNA synthesis reaction into one homogeneous assay where all of the steps of the assay can occur in one tube. There are a number of difficulties to overcome with such an approach. NESA involves cutting the DNA with a nicking endonuclease and so any nicking endonucease sites in the DNA could be cut, including the site used to detect the amplified DNA. In addition, the presence of large amounts of double-stranded DNA in the reaction could decrease the activity of the enzyme at its specific site due to competition from nonspecific sites. The reactions also have different temperature optimums. Perhaps the biggest problem is the generation of double stranded DNA at the target site. This would prevent the NESA probe from binding and giving a signal.

In the method according to the present invention, DNA synthesis and NESA may occur either serially or at the same time. Cleavage of double stranded DNA at the detection site may be inhibited by, for example, preventing formation of double stranded DNA or ensuring efficient priming immediately upstream of the target sequence so that newly synthesized DNA is itself displaced as single stranded DNA by the next round of DNA synthesis before cleavage can occur. To prevent the circularized DNA from being nicked, the initiating oligonucleotide may be synthesized with modifications that prevent cleavage. For instance, an insertion of a phosphorothioate bond at the cleavage site provides the circular oligonucleotide resistance to cleavage by an NE.

Also, DNA synthesis and NESA reaction conditions may be designed to be compatible. For example, any NE may be used to allow a wide range of reaction conditions and compatibility with a DNA polymerase. Optionally, a DNA ligase may be used even though it is incompatible with the strand displacement amplification and the NESA reaction due to temperature optimums. For example, the reaction may be initially performed at 25° C. and then raised to be compatible with the polymerase and the NE.

For each method according to the present invention, a kit is provided. The kit may comprise all the reagents useful for the method. For example, the kit may comprise all oligonucleotides, a target polynucleotide, a DNA polymerase suitable for extending an initiating oligonucleotide using a target DNA polynucleotide as a template, a reverse transcriptase for extending an initiating oligonucleotide using a target RNA polynucleotide as a template, a DNA Ligase (e.g. T4 ligase), a DNA polymerase suitable for strand displacement synthesis using a circular oligonucleotide as a template in a compatible buffer containing deoxynucleotides, one or more NEs, a DNA probe capable of hybridizing to the sequence in a synthesized DNA having a sequence corresponding to a target sequence and an NE site. Preferably, the kit comprises the initiating oligonucleotide, the DNA polymerase, the DNA synthesis primer, the probe and the NE.

The term "about" as used herein, when referring to a measurable value such as an amount, a percentage, and the like, is meant to encompass variations of ±20%, ±10%, more preferably ±5%, even more preferably ±1%, and still more preferably ±0.1% from the specified value, as such variations are appropriate.

Example 1. Polymerase Driven NESA

A polymerase drive NESA reaction was carried in this study using the following method for ligation and primer directed MDA amplification:

Ligation
    Mix 2 pM 1283 bp PCR product (10.8 µl) add 20 pM initiating oligonucleotide (2 µl 10 µM initiating oligonucleotide)
    incubate it at 95° C. for 3 min
    In a total volume 25 µl
    To the PCR and Initiating primer product mixed and denatured add
        2.5 µl Klenow 10× buffer
        2.5 µl T4 Ligase 10× buffer
        1 µl dNTPs in 10 µM concentration
        1 µl Klenow fragment (NEB cat #M0212)
        1 µl T4 Ligase (NEB cat# M0202T)
        4.2 µl molecular grade $H_2O$
    Incubate the mixture at 37° C. for 5 min and followed by heat inactivation at 72° C. for 20 min Primer Directed MDA Amplification
    Total volume 50 µl
    From the Klenow/Ligated loop primer and PCR target
    Take 5 µl DNA
    Add 5 µl denaturing buffer from the Repli-g Qiagen kit (Cat. #: 150043)
    Incubate for 3 min at room temperature
    Add 10 µl neutralizing buffer from the Repli-g Qiagen kit, vortex
    Add
        5.8 µl (10 µM concentration) primer (#M13)
        5 µl 10× buffer Buffer
        5 µl dNTPs from 10 uM stock
        5 µl Glycerol from 50% stock solution
        1 µl polymerase Phi29

2 µl Yeast Pyrophosphatase (0.01 units/µl concentration)
6.2 µl molecular grade H₂O
Vortex
Incubate at 30° C. for 16 hrs
65° C. for 3 min
4° C.
10×MDA Buffer:
500 mM Tris-HCl pH 7.5
100 mM MgCl₂
200 mM Ammonium Sulfate
1 mg/ml BSA
DNA Used

| | | |
|---|---|---|
| Initiating primer (synthetic) | [Phos]GGTGTCCCCTTGTCAGGGACTCGTA AAACGACGGCCAGTCGACACGAATTCATTGA CAGGATCTTACGAAACTTTCGGCTTTTGTAA AACGACGGCCAGTGGATTGCGAAAGAGCAAG TCTTCCT | SEQ ID NO: 1 |
| Reverse PCR primer (synthetic) | GATCCGAACGGAACGAGACA | SEQ ID NO: 2 |
| Forward PCR primer (synthetic) | CGTTGCTCAGCGACAGGATA | SEQ ID NO: 3 |
| DNA synthesis primer (synthetic) | ACTGGCCGTCGTTTT*A*C *, phosphorothioate bond | SEQ ID NO: 4 |
| Chlamydia trachomatis genomic DNA isolated from C. trachomatis | (used with PCR primers to give target DNA) | |

Figure 5:
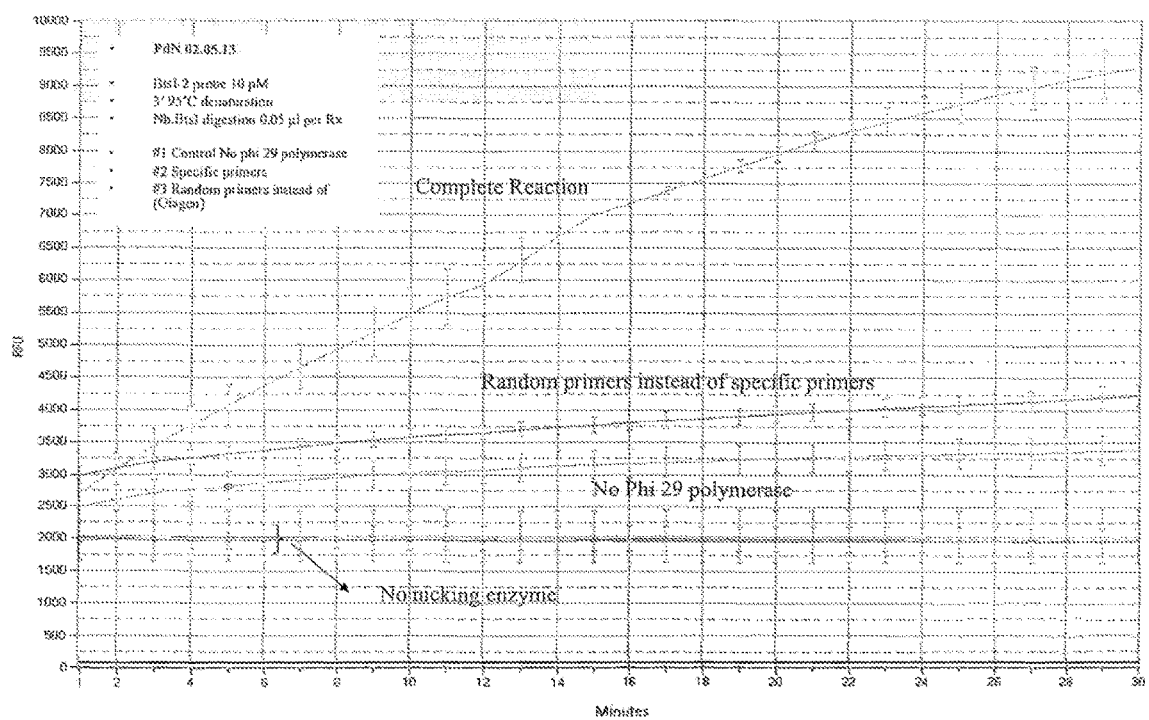
FIG. 5 shows the results of a polymerase driven NESA reaction.

FIG. 5 shows the results of the polymerase driven NESA reaction. The complete reaction (green line) contains target DNA (a PCR amplified target DNA), initiating oligonucleotide, primers, phi 29 polymerase and necessary buffers. Relative fluorescence units (y-axis) accumulating from the use of a complementary fluor-quench NESA probe specific to the target DNA are shown with time (X-axis). Nicking enzyme is required for activity, green line. Phi 29 polymerase is required for efficient detection, yellow line. Specific primers, as opposed to random primers, give greatly increased activity.

What is claimed:

1. A method for detecting a target polynucleotide in a sample, wherein the target polynucleotide comprises a target sequence flanked by a first hybridization sequence and a second hybridization sequence, wherein the target polynucleotide sequence does not comprise a nicking endonuclease (NE) recognition sequence, the method comprising
(a) exposing the target polynucleotide to an initiating oligonucleotide comprising (i) a 5' end sequence complementary to the first hybridization sequence, (ii) a 3' end sequence complementary to the second hybridization sequence, and (iii) a DNA synthesis primer recognition sequence located between the 5' end sequence and 3' end sequence, thereby forming a complex comprising the target polynucleotide and the initiating oligonucleotide, wherein the initiating oligonucleotide does not comprise a NE recognition/cutting sequence complementary to the NE recognition sequence, wherein the complex comprises a first hybridization region formed between the 5' end sequence and the first hybridization sequence and a second hybridization region formed between the 3' end sequence and the second hybridization sequence, wherein the initiating oligonucleotide comprises one or more mismatched bases with the target polynucleotide in the first hybridization region or the second hybridization region and the DNA synthesis primer recognition sequence does not hybridize to the target polynucleotide sequence in the complex;
(b) generating an extended sequence by extending the initiating oligonucleotide in the complex, wherein the extended sequence is complementary to the target sequence;
(c) forming a circular oligonucleotide in the complex by ligating the initiating oligonucleotide sequence with the extended sequence such that a NE recognition/cutting sequence is formed by the initiating oligonucleotide sequence and the extended sequence in the circular oligonucleotide, wherein the NE recognition/cutting sequence comprises the one or more mismatched bases;
(d) generating a synthesized DNA by exposing the circular oligonucleotide in the complex to a DNA polymerase and a DNA synthesis primer, wherein the DNA synthesis primer has a sequence complementary to the DNA synthesis primer recognition sequence, wherein the synthesized DNA is complementary to the circular oligonucleotide and comprises a sequence identical to the target sequence, a sequence complementary to the DNA synthesis primer recognition sequence, and the NE recognition sequence;
(e) forming a double stranded DNA by exposing the synthesized DNA to a probe having the NE recognition/cutting sequence, wherein the double stranded DNA comprises a full NE recognition site formed by the NE recognition/cutting sequence in the probe and the NE recognition sequence in the synthesized DNA;
(f) exposing the double stranded DNA to a nicking endonuclease (NE), wherein the NE is capable of recognizing the full NE recognition site and cleaving the NE recognition/cutting sequence in the full NE recognition site such that a cleaved probe is generated by cleaving the probe in the double stranded DNA with the NE and a dissociated synthesized DNA is generated by dissociating the synthesized DNA in the double stranded DNA from the cleaved probe and wherein the dissociated synthesized DNA comprises the sequence identical to the target sequence; and
(g) detecting the cleaved probe;
wherein the presence of the cleaved probe indicates the presence of the target polynucleotide in the sample.

2. The method of claim 1, wherein the target polynucleotide is a single stranded DNA.

3. The method of claim 1, wherein the sample is a biological or environmental sample.

4. The method of claim 1, wherein the NE recognition/cutting sequence spans the extended sequence and the initiating oligonucleotide sequence in the circular oligonucleotide.

5. The method of claim 1, wherein the NE is selected from the group consisting of Nb.BbvCI, Nb.BsmI, Nb.BsrDI, Nb.BtsI, nb.Bpu10I, nt.Bpu10I, Nt.AlwI, Nt.BbvCI, Nt.BsmAI, Nt.BspQI, Nt.BstNBI, Nt.CviPII, nt.BSPD6I, N.BbvC IA, N.BbvC IB, N.Bst9I, NMlyI, N.SapI, N.BseYI, N.BfiI, NB.mrI, N.FokI, V.BtsCI, N.BspD6I, N.Mva1269I, N.BsrI, R.BbvCI, Nb.SapI-1 (variant 33), Nb.SapI-1, and nt.CvQXI.

6. The method of claim 1, wherein the target polynucleotide is a DNA, and wherein the initiating oligonucleotide is extended by a DNA polymerase.

7. The method of claim 1, wherein the target polynucleotide is a RNA, and wherein the initiating oligonucleotide is extended by a RNA reverse transcriptase.

8. The method of claim 1, wherein the initiating oligonucleotide has a 5' phosphate.

9. The method of claim 1, wherein the initiating oligonucleotide has a 5' nucleotide capable of being modified to a 5' phosphate.

10. The method of claim 1, wherein the initiating oligonucleotide comprises a DNA polymerase stop site.

11. The method of claim 10, wherein the DNA polymerase stop site is a RNA linker, a synthetic linker or a modified base.

12. The method of claim 1, further comprising modifying the DNA synthesis primer, whereby the DNA synthesis primer is resistant to exonuclease degradation.

13. The method of claim 1, wherein the NE recognition sequence in the synthesized DNA overlaps with the sequence complementary to the DNA synthesis primer recognition sequence.

14. The method of claim 1, wherein steps (a)-(g) are carried out in a homogenous mixture.

15. The method of claim 1, further comprising repeating steps (e)-(g).

16. The method of claim 1, wherein the target sequence does not comprise the NE recognition/cutting sequence, and the initiating oligonucleotide does not comprise the NE recognition sequence.

* * * * *

SEQUENCE LISTING

<160> NUMBER OF SEQ ID NOS: 4

<210> SEQ ID NO 1
<211> LENGTH: 125
<212> TYPE: DNA
<213> ORGANISM: Artificial Sequence
<220> FEATURE:
<223> OTHER INFORMATION: Synthetic

<400> SEQUENCE: 1
ggtgtcccct tgtcagggac tcgtaaaacg acggccagtc gacacgaatt cattgacagg    60
atcttacgaa actttcggct tttgtaaaac gacggccagt ggattgcgaa agagcaagtc   120
ttcct                                                               125

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gatccgaacg gaacgagaca                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cgttgctcag cgacaggata                                                20

<210> SEQ ID NO 4
<211> LENGTH: 17
<212> TYPE: DNA

```
<213> ORGANISM: Artificial Sequence
<220> FEATURE:
<223> OTHER INFORMATION: Synthetic

<400> SEQUENCE: 4
actggccgtc gttttac                                                    17
```